United States Patent
Komori

(10) Patent No.: US 11,493,485 B2
(45) Date of Patent: Nov. 8, 2022

(54) SAMPLE INJECTION DEVICE

(71) Applicant: SHIMADZU CORPORATION, Kyoto (JP)

(72) Inventor: Yuki Komori, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 38 days.

(21) Appl. No.: 17/255,247

(22) PCT Filed: Aug. 6, 2018

(86) PCT No.: PCT/JP2018/029380
§ 371 (c)(1),
(2) Date: Dec. 22, 2020

(87) PCT Pub. No.: WO2020/031226
PCT Pub. Date: Feb. 13, 2020

(65) Prior Publication Data
US 2021/0270782 A1    Sep. 2, 2021

(51) Int. Cl.
*G01N 30/18* (2006.01)
*G01N 30/24* (2006.01)
*G01N 35/10* (2006.01)

(52) U.S. Cl.
CPC ............. *G01N 30/18* (2013.01); *G01N 30/24* (2013.01); *G01N 35/10* (2013.01); *G01N 2035/1027* (2013.01)

(58) Field of Classification Search
CPC .......... B01L 3/02; B01L 3/021; B01L 3/0279; B01L 3/0275; B01L 3/0255; B01L 3/0203; B01L 3/0224; B01L 3/0231; B01L 3/0234; B01L 3/10; B01L 3/0282; B01L 3/0286; B01L 3/0289; B01L 9/54; B01L 13/00;
(Continued)

(56) References Cited

U.S. PATENT DOCUMENTS 5,811,306 A * 9/1998 Komatsu .......... G01N 35/00029
73/864.22
5,879,944 A     3/1999 Komatsu
(Continued)

FOREIGN PATENT DOCUMENTS

JP    04-344032 A    11/1992
JP     9-72920 A     3/1997
(Continued)

OTHER PUBLICATIONS

Hiroshi Utsugi et al., "Surface properties and modification of powder", Journal of Powder Technology, issued: Mar. 10, 1992, published: Apr. 30, 2010, p. 161, vol. 29. No. 3.
(Continued)

*Primary Examiner* — John Fitzgerald
*Assistant Examiner* — Truong D Phan
(74) *Attorney, Agent, or Firm* — Sughrue Mion, PLLC

(57) ABSTRACT

A sample injection device (100) includes a tubular suction and discharge unit (23) configured to suction a liquid sample (S), contain the sample therein, and discharge the suctioned sample, and at least a portion of an inner wall (23*a*) of the suction and discharge unit, the portion having the sample contained therewithin, is subjected to a surface treatment (V) to increase an interfacial tension (F) that acts between the inner wall and the sample.

9 Claims, 4 Drawing Sheets

(58) Field of Classification Search
CPC .. B01L 13/02; B01L 2200/00; B01L 2200/02; B01L 2200/021; B01L 2200/022; B01L 2200/023; B01L 2200/025; B01L 2200/04; B01L 2200/026; B01L 2200/027; B01L 2200/028; A61B 10/02; A61J 1/20; A61M 37/00; G01N 2035/102; G01N 2035/1027; G01N 30/18; G01N 30/24; G01N 35/10; G01N 35/1016; G01N 35/1081; D04B 15/14
See application file for complete search history.

(56) References Cited

U.S. PATENT DOCUMENTS

| | | | | |
|---|---|---|---|---|
| 2012/0048676 A1* | 3/2012 | Giribona | ............... | B65B 3/003 198/346.2 |
| 2012/0149039 A1* | 6/2012 | Becchi | ............... | G01N 35/10 435/7.92 |
| 2019/0040714 A1* | 2/2019 | Fripp | ............... | E21B 43/12 |

FOREIGN PATENT DOCUMENTS

| | | | |
|---|---|---|---|
| JP | 2004-136236 A | | 5/2004 |
| JP | 2005-181143 A | | 7/2005 |
| JP | 2011-058901 A | | 3/2011 |
| JP | 2014050647 A | * | 3/2014 |
| JP | 2015-190864 A | | 11/2015 |
| JP | 2017-207392 A | | 11/2017 |
| JP | 2018-040682 A | | 3/2018 |
| JP | 2018040682 A | * | 3/2018 |

OTHER PUBLICATIONS

Hamilton, "Microlab 600 Series: Automated Intelligent Diluting and Dispensing", Jun. 12, 2018, pp. 1-8.
International Search Report of PCT/JP2018/029380 dated Nov. 6, 2018 [PCT/ISA/210].
Written Opinion of PCT/JP2018/029380 dated Nov. 6, 2018 [PCT/ISA/237].

* cited by examiner

FIG.7 (MODIFIED EXAMPLE)
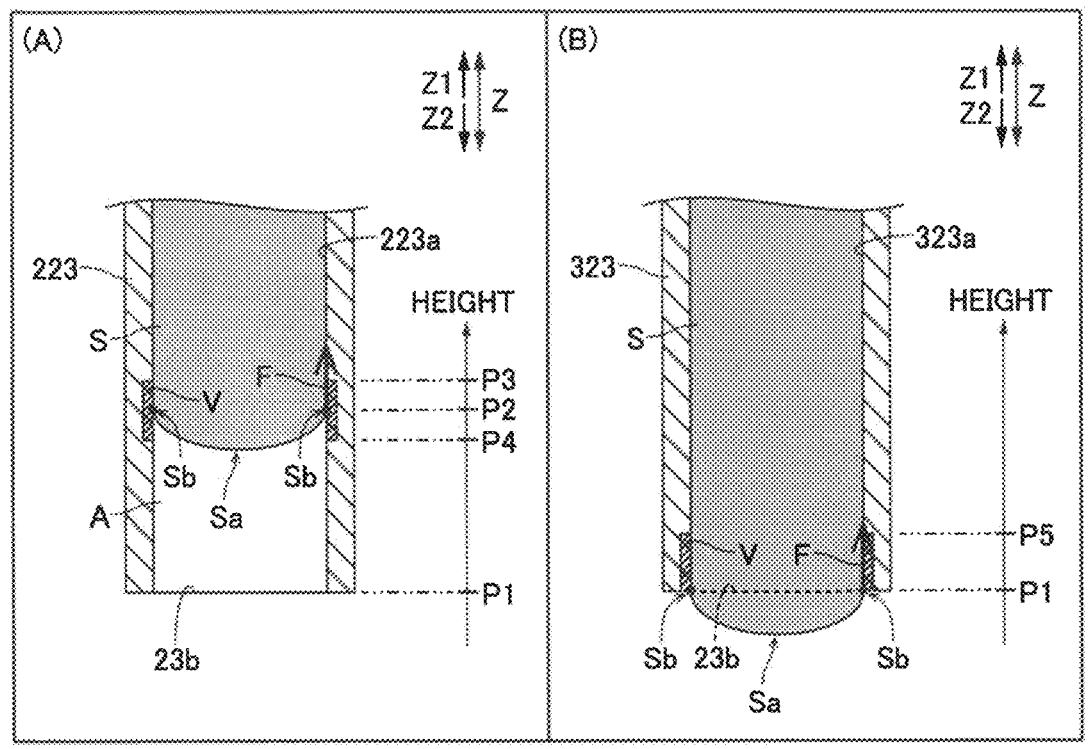
FIG.8 (MODIFIED EXAMPLE)
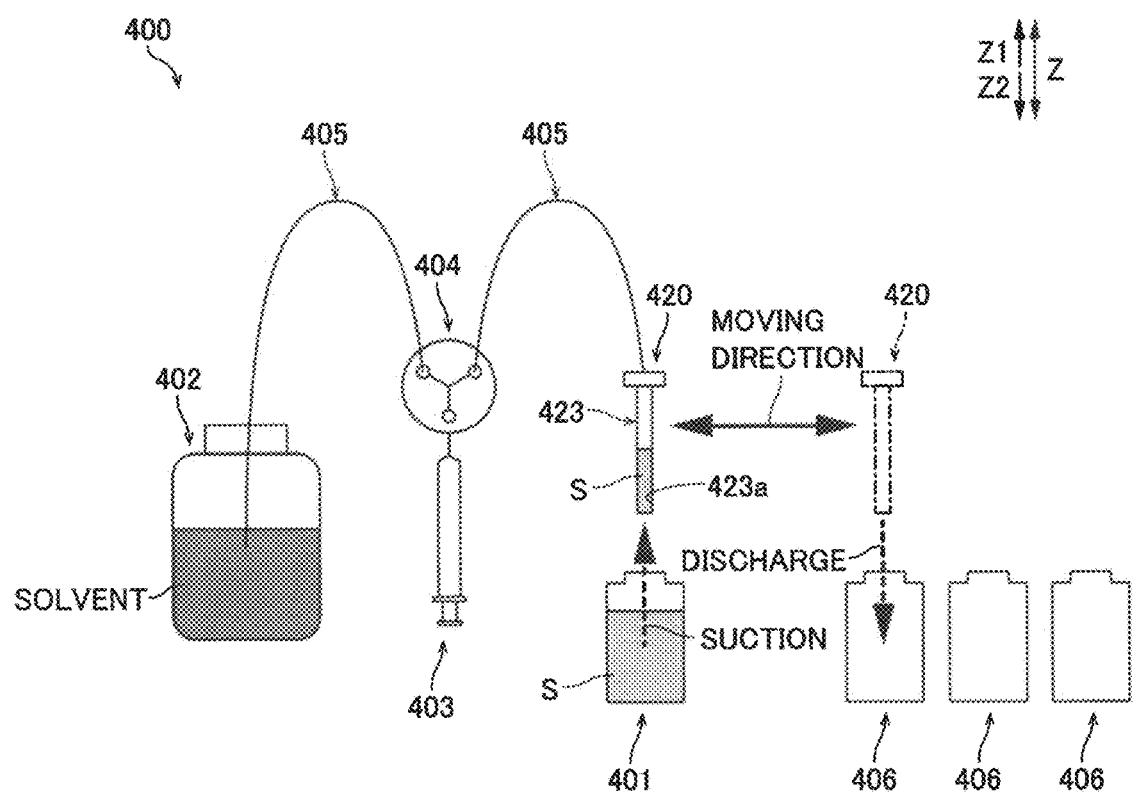

SAMPLE INJECTION DEVICE

CROSS REFERENCE TO RELATED APPLICATIONS

This application is a National Stage of International Application No. PCT/JP2018/029380, filed Aug. 6, 2018.

TECHNICAL FIELD

The present invention relates to a sample injection device, and more particularly, it relates to a sample injection device including a tubular suction and discharge unit configured to suction a liquid sample, contain the liquid sample therein, and discharge the suctioned sample.

BACKGROUND ART

Conventionally, a sample injection device including a tubular suction and discharge unit configured to suction a liquid sample, contain the liquid sample therein, and discharge the suctioned sample is known (see Patent Document 1, for example).

Patent Document 1 discloses a sample injection device for a gas chromatograph device including a syringe (cylindrical cylinder) configured to introduce a sample into the gas chromatograph device and a turret (placement table) on which a plurality of vials (bottles) that each contain a liquid sample are placed. The sample injection device described in Patent Document 1 includes a syringe drive configured to move the syringe in an upward-downward direction, a plunger (rod-shaped piston) reciprocally driven in the syringe, and a needle (suction and discharge unit) provided at the tip end of the syringe and including a flow passage therein. The sample injection device described in Patent Document 1 is configured to suction a liquid sample into the syringe and discharge the suctioned sample into the syringe via the needle by driving the plunger. Furthermore, the sample injection device described in Patent Document 1 includes a turret drive configured to move the turret in a horizontal direction such that each of the vials placed on the turret is located below the syringe.

In the sample injection device described in Patent Document 1, after the turret is horizontally moved to under the syringe by the turret drive, the syringe is moved downward by the syringe drive until the needle enters the sample in the vial placed on the turret. Then, the plunger is driven to suction the sample into the syringe via the needle to contain the sample, and then the syringe is moved to above the vial. Then, the turret is horizontally moved from under the syringe to a region other than under the syringe by the turret drive, and then the syringe is moved downward toward the gas chromatograph device arranged below the syringe drive by the syringe drive. Then, the needle is caused to penetrate a septum (lid made of rubber) of a sample introduction portion of the gas chromatograph device, and the plunger is driven in a state in which the tip end of the needle has entered the sample introduction portion such that the sample in the syringe is discharged to the outside of the syringe via the needle and is injected into the sample introduction portion of the gas chromatograph device.

PRIOR ART

Patent Document

Patent Document 1: Japanese Patent Laid-Open No. 2015-190864

SUMMARY OF THE INVENTION

Problem to be Solved by the Invention

Although not clearly described in Patent Document 1, in a conventional sample injection device as described in Patent Document 1, a sample is suctioned into a syringe via a needle in a state in which the needle has entered the sample in a vial, and thus a flow passage in the needle (suction and discharge unit) is conceivably filled with the sample (the sample conceivably exists from the base of the flow passage to the tip end of the flow passage). When the syringe (needle) is moved in an upward-downward direction in this state, in addition to gravity that acts on the sample in the flow passage, a downward force is generated on the sample in the flow passage of the needle due to the acceleration or deceleration of the syringe (needle), and thus the sample in the flow passage of the needle may conceivably be discharged to the outside from the tip end of the needle. Therefore, in the conventional sample injection device as described in Patent Document 1, when the syringe (needle) is moved with the liquid sample contained in the syringe (needle), the sample contained in the needle (suction and discharge unit) may disadvantageously be dripped (dropped) from the needle (suction and discharge unit).

The present invention is intended to solve the above problem. The present invention aims to provide a sample injection device capable of significantly reducing or preventing dripping (dropping) of a sample contained in a suction and discharge unit from the suction and discharge unit even when the suction and discharge unit is moved.

Means for Solving the Problems

In order to attain the aforementioned object, a sample injection device according to an aspect of the present invention includes a tubular suction and discharge unit configured to suction a liquid sample, contain the sample therein, and discharge the suctioned sample, and at least a portion of an inner wall of the suction and discharge unit, the portion having the sample contained therewithin, is subjected to a surface treatment to increase an interfacial tension that acts between the inner wall and the sample.

In the sample injection device according to this aspect of the present invention, as described above, at least the portion of the inner wall of the suction and discharge unit, within which the sample is contained, is subjected to the surface treatment to increase the interfacial tension that acts between the inner wall and the sample. The interfacial tension is generally a force that acts to reduce an interface (an area in which any two of a liquid, a gas, and a solid contact), and thus the interfacial tension that acts between the inner wall and the sample acts in a direction in which an interface between the inner wall and the sample is reduced.

Accordingly, in the portion of the inner wall that has been subjected to the surface treatment, the interfacial tension that acts between the inner wall and the sample is increased such that a force that acts in the direction in which the interface between the inner wall and the sample is reduced can be increased. That is, a force that acts in a direction in which the sample is kept in the suction and discharge unit can be increased such that the interface between the inner wall and the sample is reduced. For example, when the tubular suction and discharge unit is arranged along a vertical direction with the sample contained therein, the interfacial tension that acts between the inner wall and the sample acts in an upward direction opposite to a downward direction in which the sample drips due to gravity such that the interface between the inner wall and the sample is reduced. Consequently, discharge of the sample to the outside of the suction and discharge unit can be significantly reduced or prevented, and thus dripping (dropping) of the sample contained in the suction and discharge unit from the suction and discharge unit can be significantly reduced or prevented.

In the aforementioned sample injection device according to this aspect, the suction and discharge unit is preferably configured to suction the sample such that a lower end contact position of a lower end of the sample that contacts the inner wall is located at a second height above a first height at which an opening is provided at a tip end of the suction and discharge unit in a state in which the suction and discharge unit is arranged along a vertical direction, and at least a portion of the inner wall near the second height is preferably subjected to the surface treatment. Accordingly, the lower end contact position is located above a position at which the opening is provided at the tip end of the suction and discharge unit, and thus even when a downward force acts on the sample contained in the suction and discharge unit due to movement of the suction and discharge unit, for example, such that the lower end contact position moves downward, the possibility that the lower end contact position reaches the outside of the suction and discharge unit can be significantly reduced or prevented. Consequently, as compared with a case in which the lower end contact position is located at the position at which the opening is provided at the tip end of the suction and discharge unit, for example, discharge of the sample to the outside of the suction and discharge unit can be further significantly reduced or prevented, and thus dripping (dropping) of the sample contained in the suction and discharge unit from the suction and discharge unit can be further significantly reduced or prevented. Note that the portion of the inner wall near the second height includes both a portion of the inner wall at the second height and the portion of the inner wall near the second height.

In this case, the surface treatment is preferably applied from at least a portion of the inner wall near the first height to at least the portion of the inner wall near the second height. Accordingly, even when a downward force acts on the sample contained in the suction and discharge unit due to movement of the suction and discharge unit, for example, such that the lower end contact position moves downward, the lower end contact position can be reliably located in the portion that has been subjected to the surface treatment.

In the aforementioned configuration in which at least the portion of the inner wall near the second height is subjected to the surface treatment, the suction and discharge unit is preferably configured to suction the sample until the lower end contact position reaches near the first height, and then suction air until the lower end contact position reaches the second height. Accordingly, the lower end contact position can be moved upward by the amount of suctioned air, and thus the lower end contact position can easily reach the second height from the first height.

The aforementioned configuration in which at least the portion of the inner wall near the second height is subjected to the surface treatment preferably further includes a moving mechanism configured to move, in at least one of a horizontal direction or the vertical direction, the suction and discharge unit that has contained the suctioned sample therein, and the moving mechanism is preferably configured to move the suction and discharge unit in a state in which the lower end contact position is located at the second height. Accordingly, when the suction and discharge unit is moved, the lower end contact position is located at the second height, and thus the suction and discharge unit can be moved while dripping (dropping) of the sample contained in the suction and discharge unit from the suction and discharge unit is significantly reduced or prevented.

In the aforementioned sample injection device according to this aspect, the sample preferably includes an organic solvent, and the surface treatment preferably includes a treatment to enhance an oil repellency of the inner wall. Accordingly, at an interface between an oil repellent substance and an oil-based substance, an interfacial tension acts in a direction in which the interface is reduced, and thus the oil repellency of the inner wall is enhanced such that the interfacial tension that acts between the oil-based organic solvent and the oil repellent inner wall can be easily increased.

In this case, the treatment to enhance the oil repellency of the inner wall preferably includes a treatment to arrange a hydrophilic functional group on the inner wall. Accordingly, the oil repellency is enhanced in a portion in which the hydrophilic functional group is arranged, and thus the oil repellency of the inner wall can be easily enhanced by the treatment to arrange the hydrophilic functional group on the inner wall.

In the aforementioned sample injection device according to this aspect, the suction and discharge unit preferably includes a needle attached to a front end of a syringe configured to contain the sample therein, and at least a portion of an inner wall of the needle, the portion having the sample contained therewithin, is preferably subjected to the surface treatment.

Accordingly, when the needle is moved, dripping (dropping) of the sample contained in the needle from the needle can be significantly reduced or prevented. Consequently, the sample injection device capable of significantly reducing or preventing the dripping (dropping) can be applied to a configuration including the needle such as a sample injection device for a gas chromatograph device.

In this case, the needle is preferably configured to be removable from the syringe, and the needle is preferably configured to be replaceable with a needle that has been subjected to a different surface treatment according to a type of the sample. Accordingly, the needle removable from the syringe can be replaced with a needle in which an interfacial tension that acts between the sample and the inner wall of the needle is appropriate according to the properties of the sample, and thus dripping (dropping) of a different type of sample contained in the needle from the needle can be significantly reduced or prevented.

Effect of the Invention

According to the present invention, as described above, it is possible to significantly reduce or prevent dripping (dropping) of the sample contained in the suction and discharge unit from the suction and discharge unit even when the suction and discharge unit is moved.

(A) and (B) of FIG. 7 are enlarged sectional views of a needle in a sample injection device according to a modified example of the present invention.

FIG. 8 is a diagram showing the overall configuration of a sample injection device according to a modified example of the present invention.

MODES FOR CARRYING OUT THE INVENTION

An embodiment embodying the present invention is hereinafter described on the basis of the drawings.

The configuration of a sample injection device 100 according to the embodiment of the present invention is now described with reference to FIGS. 1 to 6.

Figure 1:
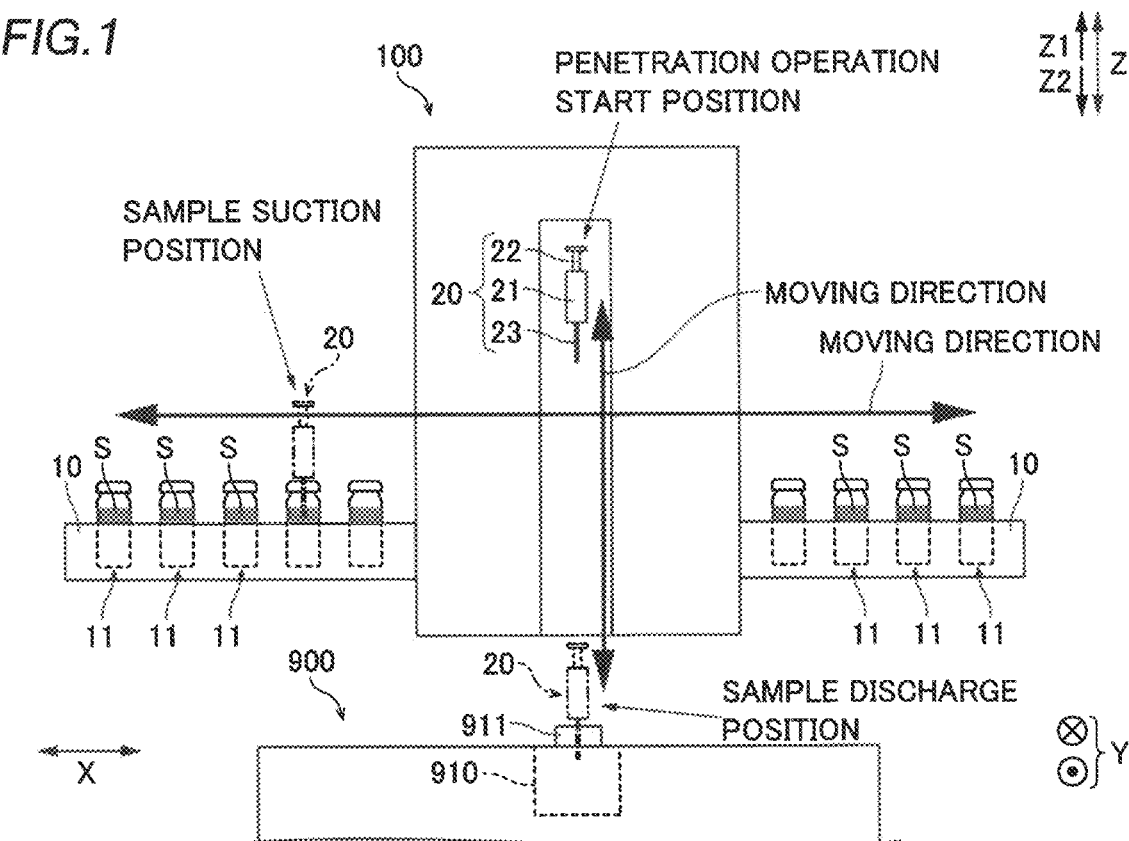
FIG. 1 is a diagram showing the overall configuration of a sample injection device according to an embodiment of the present invention.

As shown in FIG. 1, the sample injection device 100 is configured to inject a sample S into a gas chromatograph device 900 configured to analyze the sample S. The sample injection device 100 includes a turret 10 and an injector 20.

The turret 10 is a placement table on which vials 11 configured to contain the sample S, for example, are placed. A plurality of vials 11 are placed on the turret 10. In the sample injection device 100, the sample S includes an organic solvent such as hexane or acetone.

The injector 20 is configured to suction the sample S from the vials 11 that contain the sample S to be analyzed and inject the sample S into a sample introduction portion 910 of the gas chromatograph device 900. The injector 20 includes a syringe 21, a plunger 22, and a needle 23. The needle 23 is an example of a "suction and discharge unit" in the claims.

Figure 3:
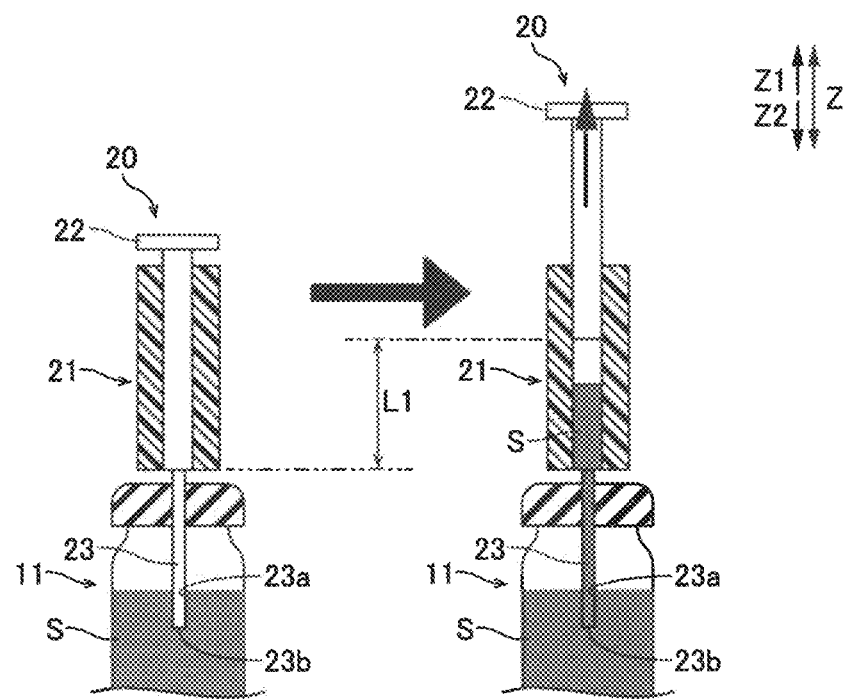
FIG. 3 is a diagram for illustrating suction of a sample by the injector.

As shown in FIG. 3, the syringe 21 has a tubular shape that extends in a vertical direction (Z direction) so as to contain the sample S therein. The plunger 22 is arranged inside the syringe 21 and is configured to be movable in the Z direction in the syringe 21.

The needle 23 is attached to the front end (Z2 side) of the syringe 21. The needle 23 includes a flow passage that extends in the Z direction therein. The flow passage of the needle 23 includes a rear end (Z1 side) connected to the syringe 21 and a front end (Z2 side) including an opening 23b. In the following description, the front end of the needle 23 may be referred to as a "tip end".

Figure 4:
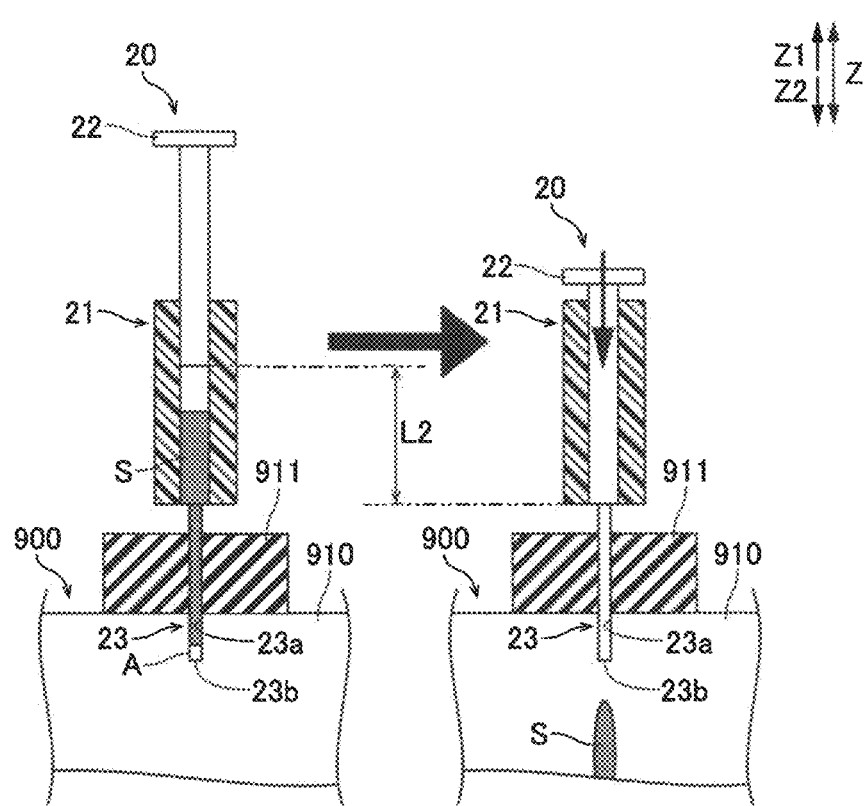
FIG. 4 is a diagram for illustrating discharge of the sample by the injector.

Thus, with the tip end (Z2 side) of the needle 23 entering the sample S, the plunger 22 is moved from the front end side (Z2 side) (a state on the left side of FIG. 3) to the rear end side (Z1 side) (a state on the right side of FIG. 3) in the syringe 21 such that the sample S can be suctioned and contained in the syringe 21 via the flow passage of the needle 23 (sample suction operation). As shown in FIG. 4, with the sample S contained in the syringe 21, the plunger 22 is moved from the rear end side (Z1 side) (a state on the left side of FIG. 4) to the front end side (Z2 side) (a state on the right side of FIG. 4) in the syringe 21 such that the sample S contained in the syringe 21 can be discharged via the flow passage of the needle 23 (sample discharge operation). As shown in FIGS. 3 and 4, in a state in which the sample S is contained in the syringe 21, the sample S is also contained in the flow passage of the needle 23.

As shown in FIG. 3, in the sample suction operation, the amount of sample S suctioned into the syringe 21 and the needle 23 is substantially equal to the volume of the syringe 21 increased by moving the plunger 22 from the Z2 side to the Z1 side. As shown in FIG. 4, in the sample discharge operation, the amount of sample S discharged from within the syringe 21 and within the needle 23 is substantially equal to the volume of the syringe 21 decreased by moving the plunger 22 from the Z1 side to the Z2 side. Note that FIGS. 3 and 4 show an example in which the plunger 22 is moved from the Z2 side to the Z1 side by a distance L1 and an example in which the plunger 22 is moved from the Z1 side to the Z2 side by a distance L2, respectively.

Figure 6:
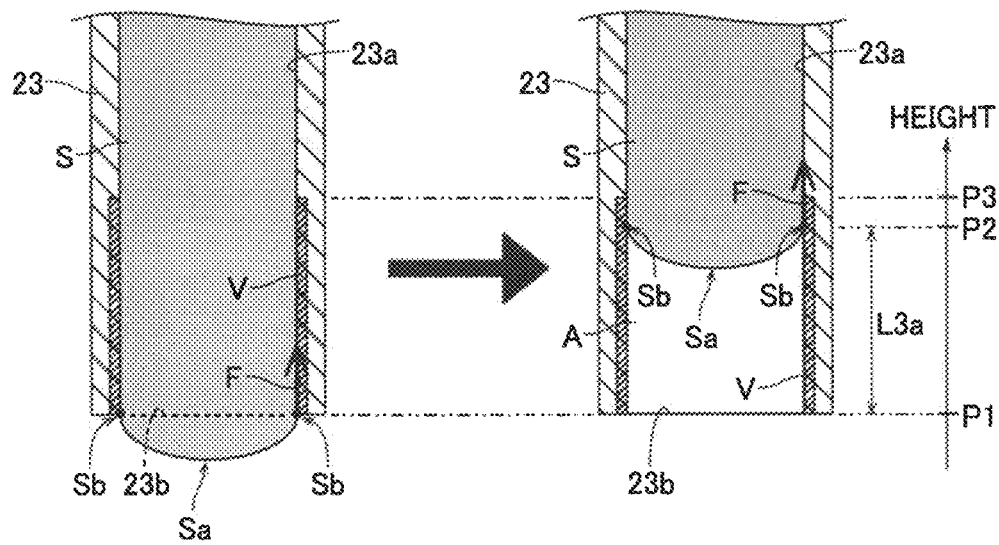
FIG. 6 is an enlarged sectional view of a needle in the injector.

In this embodiment, as shown in FIG. 6, the needle 23 is configured to suction the sample S such that a contact position Sb of the lower end Sa of the sample S that contacts the inner wall 23a is located at a height P2 above a height P1 at which an opening 23b is provided at the tip end of the needle 23 in a state in which the needle 23 is arranged along the vertical direction (Z direction). Specifically, the needle 23 is configured to suction the sample S until the contact position Sb reaches near the height P1 and then suction air A until the contact position Sb reaches the height P2. The contact position Sb is an example of a "lower end contact position" in the claims. The height P1 and the height P2 are examples of a "first height" and a "second height" in the claims, respectively.

Figure 5:
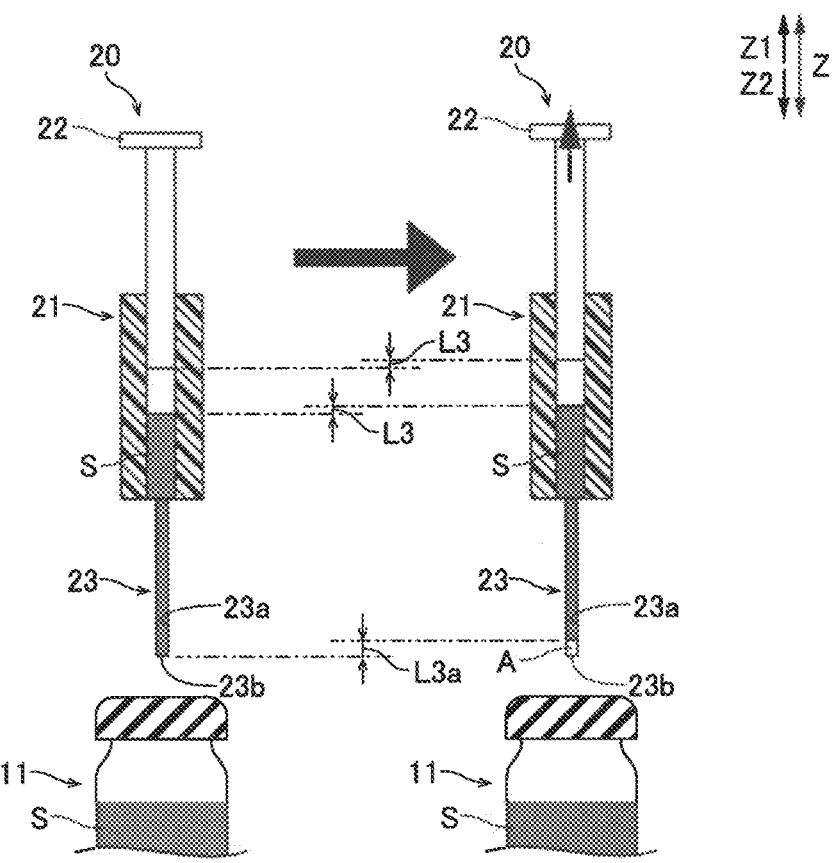
FIG. 5 is a diagram for illustrating suction of air after suction of the sample by the injector.

Specifically, as shown in FIG. 5, the injector 20 that has suctioned the sample S in the vial 11 into the syringe 21 at a sample suction position (the state of the right figure of FIG. 3) is moved in a Z1 direction by an injector drive 31 (see FIG. 2) such that the tip end of the needle 23 is spaced apart from the liquid surface of the sample S in the vial 11 (the state of the left figure of FIG. 5). Then, the plunger 22 is moved from the front end side (Z2 side) to the rear end side (Z1 side) in the syringe 21 by a predetermined distance L3. Due to this, as shown in FIG. 6, the air A is suctioned on the opening 23b side (Z1 side) at the tip end of the needle 23, and the position of the lower end Sa of the sample S is moved to the upper side (Z1 side). That is, of the lower end Sa of the sample S having a downward convex shape due to gravity, the contact position Sb that contacts the inner wall 23a of the needle 23 is moved from the height P1 at which the opening 23b is provided to the upper height P2 by a distance L3a corresponding to the distance L3.

Figure 2:
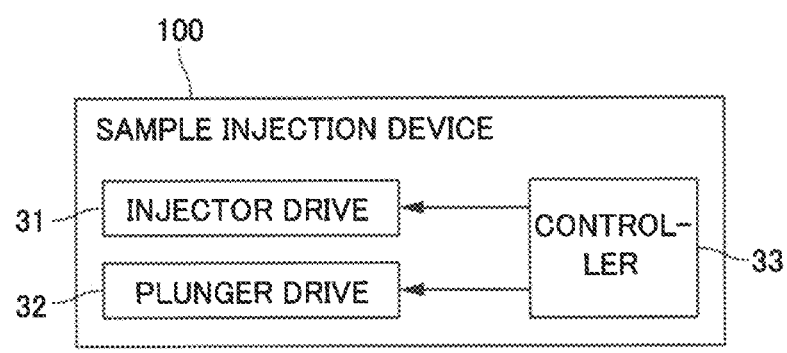
FIG. 2 is a block diagram of control of an injector control in the sample injection device according to the embodiment of the present invention.

As shown in FIG. 2, the sample injection device 100 includes the injector drive 31, a plunger drive 32, and a controller 33. The injector drive 31 is an example of a "moving mechanism" in the claims.

The injector drive 31 is configured to move the injector 20 (see FIG. 1) in a horizontal direction (X direction) and the vertical direction (Z direction) in the sample injection device 100. The injector drive 31 includes a pulse motor (not shown) that operates in synchronization with pulse power, for example.

As shown in FIG. 1, the injector drive 31 (see FIG. 2) can move the injector 20 to the sample suction position, a penetration operation start position, and a sample discharge position, for example. The "sample suction position" refers to a position at which the sample S in the vial 11 is suctioned into the syringe 21. The "penetration operation start position" refers to a position at which the penetration operation is started to cause the needle 23 to penetrate the septum 911, which is a rubber lid member (of the sample introduction portion 910), in order to inject, into the sample introduction portion 910 of the gas chromatograph device 900, the sample S suctioned into the syringe 21. The "sample discharge position" refers to a position at which the sample S in the syringe 21 is discharged in the sample introduction portion 910.

In this embodiment, as shown in FIG. 6, the injector drive 31 is configured to move the needle 23 in a state in which the contact position Sb is located at the height P2. Specifically, in the sample injection device 100, the air A is suctioned into the flow passage of the needle 23 at (in the vicinity of) the sample suction position such that the injector 20 is moved to the sample discharge position in a state in which the contact position Sb that contacts the inner wall 23a of the needle 23 has been moved to the height P2.

As shown in FIG. 2, the plunger drive 32 is configured to move the plunger 22 (see FIG. 3) in the syringe 21 (see FIGS. 3 and 4) in the vertical direction (Z direction). The plunger drive 32 includes a pulse motor (not shown) that operates in synchronization with pulse power, for example.

The controller 33 is a computer including a central processing unit (CPU), a read-only memory (ROM), a random access memory (RAM), etc. The controller 33 is configured or programmed to control the injector drive 31 and the plunger drive 32 to move the injector 20 (see FIG. 3) and the plunger 22 (see FIG. 3), respectively.

With the above configuration, the sample injection device 100 can suction the sample S in the vial 11 into the syringe 21 and introduce the suctioned sample S into the gas chromatograph device 900. As described above, the injector 20 is moved in the horizontal and vertical directions by the injector drive 31 in a state in which the sample S is contained in the syringe 21 (i.e., in a state in which the sample S is also contained in the flow passage of the needle 23). Therefore, as the injector 20 is moved, the sample S in the flow passage of the needle 23 may be discharged to the outside and dripped (dropped) from the needle 23.

Therefore, in this embodiment, as shown in FIG. 6, at least a portion of the inner wall 23a of the needle 23, within which the sample S is contained, is subjected to a surface treatment V to increase an interfacial tension F that acts between the inner wall 23a and the sample S. Specifically, the surface treatment V is applied from a portion of the inner wall 23a near the height P1 to a portion of the inner wall 23a near the height P2 so as to enhance the oil repellency of the inner wall 23a.

More specifically, in the sample injection device 100, the surface treatment V is applied from the portion of the inner wall 23a of the needle 23 at the height P1 to a portion of the inner wall 23a of the needle 23 at a height P3 near the height P2 and on the Z1 side relative to the height P2. The surface treatment V is a treatment to enhance the oil repellency by arranging hydrophilic functional groups such as hydroxyl groups or amino groups on the inner wall 23a. The surface treatment V is applied by a film treatment such as a plasma treatment or coating.

Thus, when the sample S contacts the portion of the inner wall 23a that has been subjected to the surface treatment V, a repulsive force that acts between the sample S, which includes an (oil-based) organic solvent, and the inner wall 23a, the oil repellency of which has been enhanced, increases. In other words, a force (interfacial tension) that acts to reduce an interface between the sample S and the inner wall 23a that has been subjected to the surface treatment V increases. Solid molecules cannot move, and thus the interfacial tension F causes liquid molecules to move at an interface between a solid and a liquid. For example, an upward (Z1 direction) interfacial tension F acts on the sample S at the contact position Sb corresponding to an intersection of the sample S, the air A, and the inner wall 23a. Therefore, when the interfacial tension F that acts between the sample S and the inner wall 23a increases, a force that acts to keep the sample S in the flow passage of the needle 23 increases.

In this embodiment, the needle 23 is configured to be removable from the syringe 21. That is, it is possible to replace the needle 23 with a needle 23 that has been subjected to a different surface treatment Vs according to the type of the sample S (according to the properties of each sample S).

Advantages of Embodiment

In this embodiment, the following advantages are obtained.

In this embodiment, as described above, at least the portion of the inner wall 23a of the needle 23, within which the sample S is contained, is subjected to the surface treatment V to increase the interfacial tension F that acts between the inner wall 23a and the sample S. Accordingly, in the portion of the inner wall 23a that has been subjected to the surface treatment V, the interfacial tension F that acts between the inner wall 23a and the sample S is increased such that a force that acts in a direction in which the interface between the inner wall 23a and the sample S is reduced can be increased. That is, a force that acts in a direction in which the sample S is kept in the needle 23 can be increased such that the interface between the inner wall 23a and the sample S is reduced. Consequently, discharge of the sample S to the outside of the needle 23 can be significantly reduced or prevented, and thus dripping (dropping) of the sample S contained in the needle 23 from the needle 23 can be significantly reduced or prevented.

In this embodiment, as described above, the needle 23 is configured to suction the sample S such that the contact position Sb of the lower end Sa of the sample S that contacts the inner wall 23a is located at the height P2 above the height P1 at which the opening 23b is provided at the tip end of the needle 23 in a state in which the needle 23 is arranged along the vertical direction. Furthermore, at least the portion of the inner wall 23a near the height P2 is subjected to the surface treatment V. Accordingly, the contact position Sb is located above a position at which the opening 23b is provided at the tip end of the needle 23, and thus even when a downward force acts on the sample S contained in the needle 23 due to movement of the needle 23, for example, such that the contact position Sb moves downward, the possibility that the contact position Sb reaches the outside of the needle 23 can be significantly reduced or prevented. Consequently, as compared with a case in which the contact position Sb is located at the position at which the opening 23b is provided at the tip end of the needle 23, discharge of the sample S to the outside of the needle 23 can be further significantly reduced or prevented, and thus dripping (dropping) of the sample S contained in the needle 23 from the needle 23 can be further significantly reduced or prevented.

In this embodiment, as described above, the surface treatment V is applied from the portion of the inner wall 23a near the height P1 to the portion of the inner wall 23a near the height P2. Accordingly, even when a downward force acts on the sample S contained in the needle 23 due to movement of the needle 23, for example, such that the contact position Sb moves downward, the contact position Sb can be reliably located in the portion that has been subjected to the surface treatment V.

In this embodiment, as described above, the needle 23 is configured to suction the sample S until the contact position Sb reaches near the height P1, and then suction the air A until the contact position Sb reaches the height P2. Accordingly, the contact position Sb can be moved upward by the amount of suctioned air A, and thus the contact position Sb can easily reach the height P2 from the height P1.

In this embodiment, as described above, the sample injection device 100 includes the injector drive 31 configured to move the needle 23 that has contained the suctioned sample S therein in the horizontal direction and the vertical direction. Furthermore, the injector drive 31 is configured to move the needle 23 in a state in which the contact position Sb is located at the height P2. Accordingly, when the needle 23 is moved, the contact position Sb is located at the height P2, and thus the needle 23 can be moved while dripping (dropping) of the sample S contained in the needle 23 from the needle 23 is significantly reduced or prevented.

In this embodiment, as described above, the sample S includes an organic solvent. Furthermore, the surface treatment V includes a treatment to enhance the oil repellency of the inner wall 23a. Accordingly, at an interface between an oil repellent substance and an oil-based substance, an interfacial tension F acts in a direction in which the interface is reduced, and thus the oil repellency of the inner wall 23a is enhanced such that the interfacial tension F that acts between the oil-based organic solvent and the oil repellent inner wall 23a can be easily increased.

In this embodiment, as described above, the treatment to enhance the oil repellency of the inner wall 23a includes the treatment to arrange the hydrophilic functional groups on the inner wall 23a. Accordingly, the oil repellency is enhanced in a portion in which the hydrophilic functional groups are arranged, and thus the oil repellency of the inner wall 23a can be easily enhanced by the treatment to arrange the hydrophilic functional groups on the inner wall 23a.

In this embodiment, as described above, the needle 23 is attached to the front end of the syringe 21 that contain the sample S therein. Furthermore, at least the portion of the inner wall 23a of the needle 23, within which the sample S is contained, is subjected to the surface treatment V. Accordingly, when the needle 23 is moved, dripping (dropping) of the sample S contained in the needle 23 from the needle 23 can be significantly reduced or prevented. Consequently, the sample injection device 100 capable of significantly reducing or preventing the dripping (dropping) can be applied to a configuration including the needle 23 such as a sample injection device for the gas chromatograph device 900.

In this embodiment, as described above, the needle 23 is configured to be removable from the syringe 21.

Furthermore, the needle 23 is configured to be replaceable with a needle 23 that has been subjected to a different surface treatment V according to the type of the sample S. Accordingly, the needle 23 removable from the syringe 21 can be replaced with a needle 23 in which the interfacial tension F that acts between the sample S and the inner wall 23a of the needle 23 is appropriate according to the properties of the sample S, and thus dripping (dropping) of a different type of sample S contained in the needle 23 from the needle 23 can be significantly reduced or prevented.

MODIFIED EXAMPLES

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the surface treatment V is applied from the portion of the inner wall 23a of the needle 23 at the height P1 to the portion of the inner wall 23a of the needle 23 at the height P3 has been shown in the aforementioned embodiment, the present invention is not limited to this. In the present invention, it is only required to apply the surface treatment V to at least the portion of the inner wall 23a of the needle 23 near the height P2. For example, as shown in a modified example of (A) of FIG. 7, the surface treatment V may be applied from a portion of the inner wall 223a of a needle 223 at a height P4 near a height P2 and on the Z2 side relative to the height P2 to a portion of the inner wall 223a of the needle 223 at a height P3.

While the example in which the needle 23 is configured to be moved in a state in which the contact position Sb is located at the height P2 has been shown in the aforementioned embodiment, the present invention is not limited to this. In the present invention, the needle 23 may be configured to be moved in a state in which the contact position Sb is located at the height P1. In this case, the operation of suctioning the air A until the contact position Sb reaches the height P2 after the operation of suctioning the sample S until the contact position Sb reaches near the height P1 is omitted. Alternatively, as shown in a modified example of (B) of FIG. 7, the surface treatment V may be applied from a portion of the inner wall 323a of a needle 323 at a height P1 to a portion of the inner wall 323a of the needle 323 at a height P5 near the height P1 and on the Z1 side relative to the height P1.

While the example in which the sample S includes an organic solvent, and the inner wall 23a is subjected to the surface treatment V to enhance the oil repellency of the inner wall 23a has been shown in the aforementioned embodiment, the present invention is not limited to this. In the present invention, the inner wall 23a may be subjected to a surface treatment to arrange water repellent functional groups such as alkyl groups, phenyl groups, or monoalicyclic groups when the sample is aqueous.

While the example in which the injector 20 is configured to be movable in the X and Z directions has been shown in the aforementioned embodiment, the present invention is not limited to this. In the present invention, the injector may be configured to be movable in a Y direction in addition to the X and Z directions. In this case, the samples in the vials arranged side by side in the Y direction can be suctioned into the syringe. Alternatively, the injector may be configured to be moved only in the Z direction. In this case, the turret may be moved in the horizontal direction, and the vial may be positioned under the injector such that the sample in the vial is suctioned into the syringe.

While the example in which in the sample injection device 100 configured to inject the sample S into the gas chromatograph device 900 configured to analyze the sample S, at least the portion of the inner wall 23a of the needle 23, within which the sample S is contained, is subjected to the surface treatment V to increase the interfacial tension F that acts between the inner wall 23a and the sample S has been shown in the aforementioned embodiment, the present invention is not limited to this. In the present invention, in another type of sample injection device including a tubular suction and discharge unit configured to suction a liquid sample, contain the sample therein, and discharge the suctioned sample, at least a portion of the inner wall of the suction and discharge unit, within which the sample is contained, may be subjected to the surface treatment to increase an interfacial tension that acts between the inner wall and the sample. For example, the present invention can be applied to a device (so-called diluting and dispensing device) configured to dilute and dispense a sample S in order to analyze the sample S, such as a sample injection device 400 according to a modified example shown in FIG. 8.

As shown in FIG. 8, the sample injection device 400 includes a sample vial 401, a solvent vial 402, a dilution syringe 403, a switching valve 404, and a dispensing head 420. The sample vial 401 contains a sample S to be analyzed. The solvent vial 402 contains a solvent, which is a diluent for diluting the sample S. The dilution syringe 403 is connected to the solvent vial 402 and the dispensing head 420 via tubes 405. The switching valve 404 is configured to switch a connection destination of the dilution syringe 403 to the solvent vial 402 or the dispensing head 420. A tip 423 configured to suction and contain the sample S in the sample vial 401 is detachably attached to the dispensing head 420. The tip 423 is a so-called disposable tip. The dispensing head 420 includes a pump (not shown) configured to suction the sample S into the tip 423 and discharge the sample S from the tip 423. The tip 423 is an example of a "suction and discharge unit" in the claims.

In the sample injection device 400, the sample S in the sample vial 401 is suctioned and contained in the tip 423 of the dispensing head 420, and then the sample S contained in the tip 423 is moved to the dilution syringe 403. Then, a predetermined amount of solvent in the solvent vial 402 is mixed with the sample S in the dilution syringe 403 such that the sample S is diluted to a predetermined concentration. Then, the sample S in the dilution syringe 403 is moved into the tip 423 of the dispensing head 420. Then, with the dispensing head 420 moved to a sample injection position of an analysis vial 406, the diluted sample S in the dilution syringe 403 is discharged to the analysis vial 406 via the dispensing head 420. The samples S having different concentrations are discharged into a plurality of analysis vials 406 while a concentration for diluting the sample S is changed such that the samples S having different concentrations for analysis are prepared.

In the sample injection device 400, at least a portion of the inner surface 423a of the tip 423, within which the sample S is contained, is subjected to a surface treatment V to increase an interfacial tension F that acts between the inner wall 423a and the sample S. Thus, even when the dispensing head 420 is moved, dripping (dropping) of the sample S contained in the tip 423 can be significantly reduced or prevented.

DESCRIPTION OF REFERENCE NUMERALS

21: syringe
23, 223, 323: needle (suction and discharge unit)
23a, 223a, 323a, 423a: inner wall (of the suction and discharge unit)
23b: opening (at the tip end of the suction and discharge unit)
31: syringe drive (moving mechanism)
100, 400: sample injection device
423: tip (suction and discharge unit)
P1: height (first height)
P2: height (second height)
S: sample
Sa: lower end (of the sample)
Sb: contact position (lower end contact position)
V: surface treatment (to increase an interfacial tension that acts between the inner wall and the sample)

The invention claimed is:

1. A sample injection device comprising:
   a tubular suction and discharge unit configured to suction a liquid sample, contain the sample therein, and discharge the suctioned sample; wherein
   at least a portion of an inner wall of the suction and discharge unit, the portion having the sample contained therewithin, is subjected to a surface treatment to increase an interfacial tension that acts between the inner wall and the sample; and
   the suction and discharge unit is configured to suction the sample at a position at which a tip end of the suction and discharge unit is spaced apart upward from a liquid surface of the sample such that a lower end contact position of a lower end of the sample that contacts the inner wall is located at a second height above a first height at which an opening is provided at the tip end of the suction and discharge unit, the second height at which the surface treatment is applied, in a state in which the suction and discharge unit is arranged along a vertical direction.

2. The sample injection device according to claim 1, wherein
   the sample includes an organic solvent; and
   the surface treatment includes a treatment to enhance an oil repellency of the inner wall.

3. The sample injection device according to claim 2, wherein the treatment to enhance the oil repellency of the inner wall includes a treatment to arrange a hydrophilic functional group on the inner wall.

4. The sample injection device according to claim 1, wherein
   the suction and discharge unit includes a needle attached to a front end of a syringe configured to contain the sample therein; and
   at least a portion of an inner wall of the needle, the portion having the sample contained therewithin, is subjected to the surface treatment.

5. The sample injection device according to claim 4, wherein
   the needle is configured to be removable from the syringe; and
   the needle is configured to be replaceable with a needle that has been subjected to a different surface treatment according to a type of the sample.

6. The sample injection device according to claim 1, wherein
   at least a portion of the inner wall above the second height is subjected to the surface treatment.

7. The sample injection device according to claim 6, wherein the surface treatment is applied from at least a portion of the inner wall at the first height to at least the portion of the inner wall at near the second height.

8. The sample injection device according to claim 6, wherein the suction and discharge unit is configured to suction the sample until the lower end contact position reaches the first height, and then suction air until the lower end contact position reaches the second height.

9. The sample injection device according to claim 6, further comprising:
   a moving mechanism configured to move, in at least one of a horizontal direction or the vertical direction, the suction and discharge unit that has contained the suctioned sample therein; wherein the moving mechanism is configured to move the suction and discharge unit in a state in which the lower end contact position is located at the second height.

* * * * *